US005750104A

United States Patent [19]

Sipos

[11] Patent Number: 5,750,104
[45] Date of Patent: May 12, 1998

[54] HIGH BUFFER-CONTAINING ENTERIC COATING DIGESTIVE ENZYME BILE ACID COMPOSITIONS AND METHOD OF TREATING DIGESTIVE DISORDERS THEREWITH

[75] Inventor: Tibor Sipos, Lebanon, N.J.

[73] Assignee: Digestive Care Inc., Lebanon, N.J.

[21] Appl. No.: 654,900

[22] Filed: May 29, 1996

[51] Int. Cl.$^6$ .................................................. A61K 38/43
[52] U.S. Cl. ................................................. 424/94.21
[58] Field of Search .................................... 424/94.21

[56] References Cited

U.S. PATENT DOCUMENTS

| Re. 30,910 | 4/1982 | Weigand . |
| 3,004,893 | 10/1961 | Martin . |
| 4,079,125 | 3/1978 | Sipos . |
| 4,264,583 | 4/1981 | Jandacek . |
| 4,280,971 | 7/1981 | Wischniewski et al. . |
| 4,447,412 | 5/1984 | Bilton ................................. 424/94.21 |
| 4,826,679 | 5/1989 | Roy . |
| 4,828,843 | 5/1989 | Pich et al. . |
| 4,859,471 | 8/1989 | Fullberth et al. . |
| 5,202,129 | 4/1993 | Samejima et al. . |
| 5,234,697 | 8/1993 | Sipos . |
| 5,260,074 | 11/1993 | Sipos . |
| 5,262,172 | 11/1993 | Sipos . |
| 5,302,400 | 4/1994 | Sipos . |
| 5,324,514 | 6/1994 | Sipos . |
| 5,352,460 | 10/1994 | Sipos . |
| 5,378,462 | 1/1995 | Bodecker et al. .................. 424/94.21 |
| 5,415,872 | 5/1995 | Sipos . |
| 5,460,812 | 10/1995 | Sipos . |

FOREIGN PATENT DOCUMENTS

| 1296944 | 11/1972 | United Kingdom . |
| 1362365 | 4/1974 | United Kingdom . |

OTHER PUBLICATIONS

The Journal of Pediatrics, vol. 17, No. 3, Sep. 1990:482–9, Effects of ursodeoxycholic acid therapy for liver disease associated with cystic fibrosis.

GUT, vol. 31; No. 8, 1990, 918–921, Effects of ursodeoxycholic acid treatment on nutrition and liver function in patients with cystic fibrosis and longstanding cholestasis.

Bile Acids: 1993 and The Future, Mar. 11–14, 1993, Palm Desert, Ca, Ed. C.J. Steev, J. R. Bloomer & N.F. La Russo, Univ. of Minnesota, Dept. Of Medicine, Bile Acid Therapy in the Management of Chronic Cholestasis in the Pediatric Patient.

G.J. Peschke, "Pancreatic Enzymes in Health and Disease", Springer Verlag Berlin Heidelberg, 1991, pp. 55–64.

*Primary Examiner*—Peter F. Kulkosky
*Attorney, Agent, or Firm*—Imre Balogh

[57] ABSTRACT

Disclosed are gastric acid-resistant polymer-coated buffered digestive enzymes/bile acid compositions, process for their preparations and methods of treating digestive disorders and cystic fibrosis by administering said compositions to a mammal in need of such treatment.

5 Claims, No Drawings

5,750,104

HIGH BUFFER-CONTAINING ENTERIC COATING DIGESTIVE ENZYME BILE ACID COMPOSITIONS AND METHOD OF TREATING DIGESTIVE DISORDERS THEREWITH

BACKGROUND OF THE INVENTION

1. Field of the Invention

This invention relates to excess buffer-stabilized digestive enzyme-bile acid compositions and a method for: treating digestive enzyme deficiency, digestive disorders and cystic fibrosis by administering said compositions to a mammal in need of such treatment. More particularly, the invention relates to enteric coated excess buffer-stabilized digestive enzyme-bile acid-containing compositions having reduced levels of digestive enzymes to circumvent side effects associated with high-dose of high strength lipase digestive enzymes.

2. Reported Developments (A) Pancreatic Enzymes

It is well documented in the literature that exogenously administered pancreatic enzymes from animal sources can partially remedy the enzyme deficiency caused by various diseased states of the pancreas, e.g., pancreatitis, pancreatectomy, cystic fibrosis, etc. Fewer data exist for enzymes from plant and microbial sources.

Pancreatic enzymes supplements were available in the U.S. before the passage of the 1938 Food, Drug and Cosmetic Act. As a consequence, pancreatic enzymes were and still are formulated, manufactured and sold without submitting an approved New Drug Application (NDA) containing safety, efficacy or bioavailability data. Several products with various doses of lipase with and without enteric coating are available for patients suffering from pancreatic enzyme deficiency and digestive disorders.

Pancreatic enzymes are active under near neutral and slightly alkaline conditions. Under gastric conditions, i.e., in the presence of acid and pepsin, most of the enzymes are irreversibly inactivated with resulting loss of biological activity. Lipases are the most sensitive to gastric inactivation, therefore, it is imperative that the exogenously administered enzymes be protected against gastric inactivation and remain intact during their transit through the stomach into the duodenum.

While the transit of the enzymes intact through the stomach is essential, it is another requirement for maximum efficacy that the enzymes be released in the duodenum within 5 to 30 minutes, since digestion by pancreatic enzymes and absorption of the metabolites take place primarily in the upper segment of the intestine, i.e. duodenum and upper part of the jejunum.

The normal pancreas, in response to food stimulation, gradually releases bicarbonate and digestive enzymes. The bicarbonate is released into the duodenum to neutralize the acid chyme. The enzymes are released as zymogens (inactive precursors) and are activated by enterokinase to form active enzymes, e.g., trypsin from trypsinogen. The newly activated trypsin in turn generates more active enzymes in the duodenum by an autocatalytic mechanism. Simultaneously, the activated enzymes are thoroughly mixed with the arriving food from the stomach, and digestion ensues. This process takes place as long as food is pumped from the stomach into the duodenum.

Pancreatic enzymes have been used for the past seventy years to treat various digestive disorders. The early clinical results were variable. With time it became apparent that some of the poor clinical response were due to gastric inactivation of the exogenously administered enzymes. A revived interest in enzyme-containing digestive aids occurred in the late 1950's and early 1960's, with the development of acid stable enteric coatings. This, it was believed that the detrimental effects of gastric acidity on the enzymes could be avoided by the use of such enteric coatings, and more effective enzyme therapy thus made possible. A great variety of enteric coated enzyme-containing digestive aids were marketed in this period. However, most of these products contained low levels of active enzymes, especially lipase, and often too low to effectively treat many enzyme deficiency-related conditions.

Moreover, the coatings generally failed to protect the enzymes against gastric inactivation or to release them in an activatable state in the duodenum. Thus, most enteric coatings were permeable to gastric acid and many failed to disintegrate in the duodenum under neutral conditions within a reasonable time.

Because of these known defects in the coatings as well as the low levels of enzyme activities of prior art digestive enzyme-containing compositions, it has long remained a desired goal to develop a biologically active enzyme-containing digestive aid composition that would prevent gastric acid and pepsin inactivation of the enzymes upon passage through the stomach, and, after transit from the stomach into the duodenum, would release the enzymes in a reproducible, i.e., predictable, manner within minutes in their biologically active state.

High strength pancreatic enzyme preparations were proposed by the prior art for the treatment of pancreatic enzyme insufficiency. U.S. Pat. Nos. 4,079,125 and 5,302,400 disclose enteric coated compositions containing 67–90% w/w and 65–90% w/w of pancreatic enzymes.

Pharmaceutical companies have provided enteric coated pancreatic enzyme dosages with up to 35,000 USP units/ capsule of lipase and various amylase and protease activities.

Recently, however, unexpected complications were discovered, especially in children, who developed strictures of the ascending colon and pathological changes of postischemic ulceration repair with mucosal and submucosal fibrosis when given high-dose, high-strength lipase pancreatic enzyme extracts. (See, for example, Smyth et al., "Strictures of ascending colon in cystic fibrosis and high strength pancreatic enzymes", Lancet 1994; 343:85–6; Oades et al., "High strength pancreatic enzyme supplements and large bowel stricture in cystic fibrosis", Lancet 1994; 343–109 and Campbell et al., "High strength pancreatic enzyme supplements and large bowel stricture in cystic fibrosis", Lancet 1994; 343:109–10).

Host factors also influence the bioavailability and efficacy of pancreatic enzymes which include the availability of the required alkaline pH and bile acid in the small intestine. Additional factors which compound the problem in patients with cystic fibrosis are deficiency in bicarbonate, increased small intestinal viscosity, increased presence of mucines in the small intestine, altered or deficient intraluminal bile salt concentrations, and impaired pancreatic function.

It is, accordingly, one of the objects of the present invention is to provide a pharmaceutical compositions which contains doses of pancreatic enzymes the administration and use of which in patients do not cause the aforementioned undesirable side effects.

Another object of the present invention is to address the insufficiency of bile acid and buffering capacity in the small intestine which, along with pancreatic enzyme deficiency, cause digestive disorders.

(B) Bile Acids and Buffers

It is known that bile acid, i.e. ursodiol (hereinafter sometimes referred to as UDCA or bile acid) is capable of augmenting liver function, dissolving gallstones and improving the nutritional state of patients having cystic fibrosis caused by hepatobiliary complications. See for example, Ursodeoxycholic Acid Dissolution of Gallstones in Cystic Fibrosis, Sahl, B., Howat, J., Webb, K., Thorax, 43:490–1 (1988); Effects of Ursodeoxycholic Acid Therapy for Liver Disease Associated with Cystic Fibrosis, Colombo, C., Setchell, K. D., Podda, M., Crosignani, A., Roda A., Curcio, L., Ronchi, M. and Giunta, A., The Journal of Pediatrics, 117:482–489 (1990); Effects of Ursodeoxycholic Acid Treatment on Nutrition and Liver Function in Patients with Cystic Fibrosis and Longstanding Cholestasis. Cotting, J., Lentze, M. J. and Reichen, J., Gut 31: 918–921 (1990). Also, UDCA has recently gained acceptance as an effective therapeutic modality to dissolve small to medium size cholesterol gallstones in gallstone afflicted patients. See for example, The Effect of High and Low Doses of Ursodeoxycholic Acid on Gallstone Dissolution in Humans, Salen, G., Colalillo, A., Verga, D., Bagan, E., Tint, G. S. and Shefer, S., Gastro., 78:1412–1418 (1980); Ursodeoxycholic Acid: A Clinical Trial of a Safe and Effective Agent for Dissolving Cholesterol Gallstones, Tint, G. S., Salen, G., Colalillo, A., Graber, D., Verga, D. Speck, J. and Shefer, S., Annals of Internal Medicine, 91:1007–1018 (1986); Clinical Perspective on the Treatment of Gallstones with Ursodeoxycholic Acid, Salen, G., J. Clin. Gastroenterology, 10 (Suppl. 2):S12–17 (1988); Nonsurgical Treatment of Gallstones, Salen, G. and Tint, G. S., New England J. Med., 320:665–66 (1989); and Reducing Cholesterol Levels, Weigand, A. H., U.S. Pat. No. 3,859,437. The recommended dosage is 10 to 15 mg/kg of body weight. In some patients much higher dosages (for example, about 30 mg/kg of body weight) are required to achieve limited benefits. However, in some patients undesirable side effects (such as, severe diarrhea) seriously limit the use of this drug.

Pancreatic enzymes and salts of UDCA complement one another in the digestive system of a mammal. A dietary supplement containing both the enzymes and salts of UDCA would provide in a convenient pre-determined dose the remedy needed to treat the above-described diseased states. However, the acidic form of UDCA is incompatible with pancreatic enzymes. Pancreatic enzymes/UDCA compositions have a pH of about 5 to 5.5. Under these acidic conditions most pancreatic enzymes show a low biological activity of about 10% to 40%. Lipase is especially affected by the low pH for the reasons that:

Lipase is most stable at pH 5.0 to 6.5, however, at these ph's, lipase has minimal biological activity. (Table A and Table II).

Lipase has maximum biological activity at pH 8.0 to 9.0 (Table II).

Lipase, however, is rapidly and irreversibly inactivated at pH 7.0 to 9.0 (Table A).

TABLE A

Activity and Stability of Pancreatic Lipase At Different pH's vs. Time

| TIME IN MINUTES | pH | | | | | |
|---|---|---|---|---|---|---|
| | 3.0 | 4.0 | 4.5 | 5.0 | 6.0 | 7.0 |
| 15 | 2 | 20 | 72 | 92 | 92 | 85 |
| 30 | 0 | 10 | 68 | 88 | 88 | 78 |
| 45 | 0 | 7 | 65 | 87 | 87 | 72 |
| 60 | 0 | 6 | 60 | 85 | 85 | 66 |

TABLE A-continued

Activity and Stability of Pancreatic Lipase At Different pH's vs. Time

| TIME IN MINUTES | pH | | | | | |
|---|---|---|---|---|---|---|
| | 3.0 | 4.0 | 4.5 | 5.0 | 6.0 | 7.0 |
| 90 | 0 | 5 | 52 | 80 | 80 | 55 |
| 120 | 0 | 5 | 42 | 78 | 78 | 42 |
| 150 | 0 | 4 | 38 | 75 | 75 | 34 |
| 180 | 0 | 3 | 32 | 73 | 73 | 28 |

Based on these observations, the prior art concluded that pancreatic lipase containing digestive enzyme preparation must have an acidic compositions in between the pH's of 5 to 6 to be stable.

The currently marketed pancreatic enzyme preparations support this fact since without exception, all of the currently marketed digestive enzyme preparations have an acidic pH when the composition is ground up and is dissolved in water (Table I).

Recently, it has been discovered that the enteric coating polymers employed to protect the pancreatic enzymes against gastric inactivation during gastric transit, are also acidic in nature, and require substantial quantity of base to be neutralized. For example, some of the commercially marketed products, such as CREON®, COTAZYM-S®, PANCREASE® and ULTRASE™ when ground up and dissolved in water had pH's of 5.5, 5.9 and 5.7, respectively, as shown in Table I. At these acidic pH's, lipase, an essential enzyme that is required by cystic fibrosis patients, is rendered ineffective. Therefore, in order to compensate for the acidic nature of the enteric coated polymer, one needs to include extra buffering capacity in the composition to neutralize the acidic enteric coat and provide a basic environment for lipase to exert its enzymatic activity.

TABLE I

LIPASE ACTIVITY OF PANCREATIC ENZYME-CONTAINING PRODUCTS

| PRODUCT | pH* | Label Claim | Assayed Activity at pH 9.0 | Buffering Capacity** | % Activity in the Duodenum at*** pH 6.5–7.25 | | |
|---|---|---|---|---|---|---|---|
| | | | | | 6.5 | 7.0 | 7.25 |
| PANCREASE ® | 5.9 | 4000 | 8853 | 0 | 0% | 6% | 22% |
| CREON ® | 5.5 | 8000 | 10428 | 0 | 0% | 5% | 19% |
| COTAZYME-S ® | 5.7 | 5000 | 8214 | 0 | 0% | 6% | 22% |
| ULTRASE ™ MT-20 | 5.7 | 20000 | 21375 | 0 | 0% | 5% | 20% |

*pH of Ground-Up Composition Dissolved in Distilled Water
*Buffering Capacity of Preparations to Neutralize Excess Gastric Acid to pH 7.0 in meq. (1.0 meq Bicarbonate Neutralizes 12 ml Gastric juice from pH 1.5 to pH 7.0).
***These products rely on the patient's ability to secrete sufficient bicarbonate to increase the pH of the duodenum from 6.5 to 7.25. Many C.F. patients are deficient in bicarbonate secretion and their duodenal pH's are acidic.
PANCREASE ® is a registered trademark of McNeil Pharmaceutical
CREON ® is a registered trademark of Solvay Pharmaceuticals, Inc.
COTAZYME ® is a registered trademark of Organon, Inc.
ULTRASE ™ is a registered trademark of Scandipharm, Inc.

Furthermore, recent clinical findings indicate that buffer deficiency is more serious in many patients than believed heretofore. For example, the majority of cystic fibrosis patients are deficient in bicarbonate secretion and their upper intestinal pH's are in the range of 4.5 to 6.8. Some of the alcohol induced cholestatic liver diseased patients duodenal pH's are also in the slightly acidic to neutral range, such as pH 6.0 to 7.6. Even when the pancreas and the gallbladder are maximally stimulated with secretion and cholecystokinin hormones, the intestinal pH's seldom exceed pH 7.0 in cystic fibrosis and 7.6 in alcoholic liver diseased patients.

The activity of Lipase in the pH range of 6–9 is shown in Table II.

TABLE II pH vs. Activity of Lipase

| pH  | USP Unit/mg | % Activity |
|-----|-------------|------------|
| 9.0 | 20.6        | 100        |
| 8.5 | 18.1        | 88         |
| 8.0 | 14.4        | 70         |
| 7.5 | 10.5        | 51         |
| 7.0 | 4.9         | 24         |
| 6.5 | 0.7         | 3          |
| 6.0 | 0.1         | <1         |

Because it is difficult to predict the extent of bicarbonate deficiency in these patients population without intubation and collection of intestinal juices for pH and bicarbonate assays, it is necessary to assure that adequate amount of buffer is administered with the exogenous pancreatic enzymes and bile acid compositions.

It has now been discovered that the problems associated individually with enteric coated microtablets and microspheres containing pancreatic enzymes and compositions containing UDCA, may be overcome in a dietary supplement containing both the pancreatic enzymes and a buffered UDCA composition. In accordance with the discovery, UDCA is micropulverized in the presence of a suitable buffer salt to obtain ultrafine particles that will readily dissolve in the intestinal juices under physiological conditions and provide a slightly alkaline media. The concentration of the buffer salt is adjusted to provide a 15% to 40% excess or even higher over concentration of the buffer what is required for the instant neutralization of UDCA and the acidic enteric coating in order to provide a pH range of 7 to 10 when administered to a mammal having bicarbonate insufficiency.

Pancreatic enzymes then are combined with a micropulverized and buffered-UDCA and additionally buffered with sufficient quantity of a biologically compatible, pharmaceutically acceptable buffer that prevents deactivation of the enzymes and preserves the natural biological activities of both the enzymes and the buffered-UDCA in the intestine, and thus provide sufficient buffering capacity in the duodenal microenvironment to assure maximal biological activity for lipase. The pancreatic enzyme/buffered-UDCA composition can be prepared into microtablets and microspheres in the presence of a suitable liquid without inactivation of the enzyme/bufferedUDCA composition thereby resulting in products that do not crumble upon drying or disintegrate upon initiation of the polymer coating procedure. The polymer coat protects the enzyme/buffered-UDCA composition from acid inactivation during gastric transit into the intestine.

SUMMARY OF THE INVENTION

In one aspect, the present invention provides an excess-buffer-stabilized digestive-enzyme composition in the form of microspheres or microtablets individually coated with an enteric coating and optionally provided in a capsule form so as to contain the required dosage amount for delivery to a patient.

In another aspect, the present invention provides an excess buffer-stabilized digestive enzyme-bile acid composition in the form of microspheres or microtablets individually coated with an enteric coating and optionally provided in a capsule form so as to contain the required dosage amount for delivery to a patient.

In another aspect, the present invention provides a method for: treating digestive enzyme deficiency, digestive disorders and cystic fibrosis by administering said above-described compositions to a mammal in need of such treatment.

The principal active enzymes include, but are not limited to pancreatic enzymes as (I) the proteases, for example, Trypsin, E.C. (Enzyme Commission Number) 3.4.4.4; Chymotrypsin, E.C. 3.4.4.5; Chymotrypsin B, E.C. 3.4.5.6; Pancreatopeptidase E, E.C. 3.4.4.7; Carboxypeptidase A, E.C. 3.4.2.1; and Carboxypeptidase B, E.C. 3.4.2.2; (II) the lipases, for example, Glycerol ester hydrolase (Lipase), E.C. 3.1.1.3; Phospholipase $A_2$, E.C. 3.1.1.4; and Sterol ester hydrolase, E.C. 3.1.1.13; (III) the nucleases, for example, Ribonuclease, E.C. 2.7.7.16 and Deoxyribonuclease, E.C. 3.1.4.5; and the amylase, α-Amylase, E.C. 3.2.1.1.

Generally, the enzymes are available in powder or crystalline form, typically as concentrates of pancreatic enzymes (protease, amylase, lipase and, preferably, ribonuclease) derived from animal sources (hog, sheep and bovine). Desirably, co-lipase is also included. The starting pancreatic enzyme concentrates used to make the compositions of Examples 1, 2 and 3 are the ones that contain lipase with defined strength, i.e., Pancreatin concentrate: 40 USP unit per mg of lipase activity and Pancreatin concentrate, High lipase greater than 100 USP unit per mg of lipase activity. Depending on the desired lipase activity of the final composition, one needs to use 2.5 times less of the Pancreatin concentrate, high lipase (greater than 100 USP units/mg) as compared to Pancreatin concentrate (40 USP units/mg). To assure proper therapeutic effectiveness for pancreatic enzyme deficient patients, the initial enzyme activities per milligram should be at least those set forth in the examples. In any event, for properly controlled therapy, it is important both to know the initial enzyme activities and to be able to predict the corresponding activity upon release in the intestinal tract. It should be understood that, as used herein, the term "enzyme" includes not only the already activated form but also the zymogen precursor which is capable of being transformed into the active form in mammalian intestinal fluid.

The principal buffering agents to provide a pH range of 7–10 in the microenvironment of the upper intestine include, but are not limited to: anhydrous sodium carbonate, sodium bicarbonate, potassium carbonate, potassium bicarbonate, ammonium carbonate, tromethamine, di(tris (hydroxymethyl)aminomethane)carbonate, tris-glycine, diarginine in the molecular weight range of 350 to 50,000 Daltons, tri-arginine in the molecular weight range of 350 to 50,000 Daltons, poly-arginine in the molecular weight range of 350 to 50,000 Daltons, di-lysine in the molecular weight range of 290 to 15,000 Daltons, tri-lysine in the molecular weight range of 290 to 15,000 Daltons, poly-lysine in the molecular weight range of 290 to 15,000 Daltons, diethylamine and triethanolamine.

The composition of the present invention comprises based on the total weight of the composition:

a) of from about 10 to about 70% w/w of a pancreatic enzyme;

b) of from about 0 to about 20% w/w, preferably of from about 0.1 to about 15% w/w, and most preferably of from about 0.25 to about 10% w/w of a micropulverized, buffered bile acid in powder form, said buffer/bile acid forming a mixture of a 1 to 1 neutralization equivalent ratio;

c) of from about 15 to about 60% w/w, preferably of from about 18 to about 40% w/w of a buffering agent;

d) of from about 0.5 to about 16% w/w of a disintegrant selected from the group consisting of ursodiol, starch, modified starches, microcrystalline cellulose and propylene glycol alginate;

e) of from about 1 to about 19% w/w of an adhesive polymer selected from the group consisting of polyvinylpyrrolidone, hydroxypropyl cellulose, cellulose acetate phthalate and a 60:40 blend of ethyl cellulose and hydroxypropyl methyl cellulose;

said composition is to provide a pH range of 7–10 in the microenvironment of the upper intestine when administered to a mammal having bicarbonate insufficiency;

said ingredients being formed into microspheres or microtablets which are individually coated with from about 7 to about 25% w/w of a non-porous, pharmaceutically acceptable, gastric acid-resistant polymer-coating containing of from about 0.01 to about 2% w/w of talc, said gastric acid-resistant coating is insoluble in the pH range of 1.5 to 5 but is soluble in the pH range of 5.5 to 9.

The microspheres or microtablets are placed into soft or hard-shell capsules which will contain the proper dosage for delivery to the patient.

Upon administration to the patient only the capsules disintegrate while the composition of the present invention passes through the stomach intact and is delivered into the small intestine where the coating of the microspheres/microtablets dissolves in the neutral to alkaline pH environment. The content of the microspheres/microtablets is dispersed into the content of the small intestine and delivers the high levels of biologically active digestive enzyme-bile acid and buffer composition.

In accordance with the present invention, the process of preparing the compositions is shown schematically in Table III.

TABLE III

Schematic for Enzyme Microsphere Production

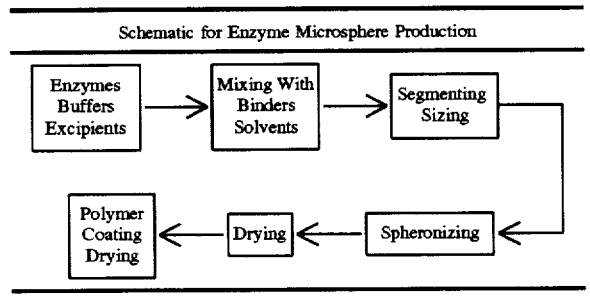

In accordance with the present invention the composition is prepared by a process comprising in detail the steps of:

a) micropulverizing a neutralizing equivalent of a buffering agent selected from the group consisting of anhydrous sodium carbonate, sodium bicarbonate, potassium carbonate, potassium bicarbonate, ammonium carbonate, tromethamine, di(tris(hydroxymethyl)amino-methane) carbonate, tris-glycine, di-arginine in the molecular weight range of 350 to 50,000 Daltons, tri-arginine in the molecular weight range of 350 to 50,000 Daltons, poly-arginine in the molecular weight range of 350 to 50,000 Daltons, di-lysine in the molecular weight range of 290 to 15,000 Daltons, tri-lysine in the molecular weight range of 290 to 15,000 Daltons, poly-lysine in the molecular weight range of 290 to 15,000 Daltons, diethylamine and triethanolamine, with a molar equivalent of a bile acid selected from the group consisting of ursodiol (UDCA or ursodeoxycholic acid), glycylursodeoxycholic acid, tauroursodeoxycholic acid, N-methylglycylursodeoxycholic acid, N-methyltauroursodeoxycholic acid, cholic acid, deoxycholic acid, chenodeoxycholic acid, glycylcholic acid, taurocholic acid, N-methylglycylcholic acid, methyltaurocholic acid, glycyldeoxycholic acid, N-methyltaurodeoxycholic acid, and N-methylglycylchenodeoxycholic acid;

b) blending dry powdery ingredients selected from the group consisting of i) from about 10 to about 70% w/w of an enzyme from the group consisting of pancreatic concentrate containing pancreatic proteases, lipases, nucleases and amylases;

ii) from about 0 to about 20% w/w, preferably from 0.1 to about 15% w/w, and most preferably from about 0.25 to about 10% w/w of the micropulverized, buffered mixture of step (a);

iii) from about 15 to about 60% w/w, preferably from about 18 to 40% w/w of a buffering agent selected from the group consisting of anhydrous sodium carbonate, sodium bicarbonate, potassium bicarbonate, potassium carbonate, ammonium carbonate, tromethamine, di(tris (hydroxymethyl)aminomethane)-carbonate, trisglycine, di-arginine in the molecular weight range of 350 to 50,000 Daltons, tri-arginine in the molecular weight range of 350 to 50,000 Daltons, poly-arginine in the molecular weight range of 350 to 50,000 Daltons, di-lysine in the molecular weight range of 290 to 15,000 Daltons, tri-lysine in the molecular weight range of 290 to 15,000 Daltons, poly-lysine in the molecular weight range of 290 to 15,000 Daltons, diethylamine and triethanolamine;

iv) from about 0.5 to about 16% w/w of a disintegrant selected from the group consisting of ursodiol, starch, modified starches, microcrystalline cellulose and propylene glycol alginate; and v) from about 1 to about 19% w/w of an adhesive polymer selected from the group consisting of polyvinylpyrrolidone, hydroxypropyl cellulose, cellulose acetate phthalate, ethyl cellulose and hydroxypropyl methyl cellulose;

c) wetting said blended ingredients with a liquid to cause the blend to stick together, wherein said liquid is selected from the group consisting of: 1%–25% w/w ethanol/ 75%–99% w/w 2-propanol/0.2%–1.0% w/w water; 98%–99% w/w 2-propanol /0.2–1% w/w water; 1%–25% w/w methanol/0.2%–1% w/w water/75%–98% w/w 2 propanol/1%–5% w/w ethylacetate;

d) granulating or extruding the liquid-wetted blend through a 1.0 or a 1.5 mm S/S screen into segmented granules;

e) converting the segmented granules to spherical particles;

f) compacting the spherical particles;

g) drying the spherical particles;

h) separating the spherical particles if not of uniform size according to desired sizes using U.S. Standard sieve screens;

i) coating the particles with a gastric acid-resistant polymer that dissolves under neutral or slightly basic conditions; and j) drying the polymer-coated spherical particles.

DETAILED DESCRIPTION OF THE INVENTION

In preparing the buffered pancreatic enzymes/bile acid-containing microspheres of the present invention utilizing the extrusion, uni-sizer and marumerization process moisture must be included in the liquid or solvent-adhesive composition to render the adhesive polymer sticky enough to bind the buffered enzymes-UDCA-containing fluffy powder into a pliable, solid mass. This prevents the crumbling of the microspheres during the drying and coating steps as well as allows the preparation of much smaller particle size microspheres, i.e. in the range of 10 to 80 mesh. Accordingly, it was found that the moisture level during the preparation of the composition should be in the range of from about 0.2% w/w to about 2.0% w/w, preferably, in the range of 0.2% w/w to 1.5% w/w, and most preferably in the range of 0.2% w/w to 1.0% w/w. When the compositions contained such amounts of moisture, the microspheres were found to be stable on aging and biological activity was preserved as long as the moisture level did not exceed about 2.0% w/w of the total composition.

The process for the manufacture of microspheres consists of:

1) Micropulverizing a neutralizing equivalent of sodium carbonate (anhydrous) or other suitable buffering agent with a molar equivalent of a bile acid in a centrifugal grinder (Brinkman, Inc.) or in an impact pulverizer or other suitable grinder at a setting of 4 and employing a 0.2 mm screen.
2) Blending the micropulverized and dried, powdery ingredients together in a conventional blender and wetting the composition with a suitable liquid composition that causes the dry blend to stick together.
3) Segmenting or extruding the liquid moistened composition through a 1.0 or a 1.5 mm S/S screen using an oscillating/reciprocating granulator or a twin-screw extruder at a medium-to-high speed.
4) Classifying the segmented (granulated) particles in a "uni-sizer vessel" that rotates at 15 to 45 rpm for about 5 to 10 minutes. (The particles in the "uni-sizer vessel" are converted from segments to a round particle shape.
5) Compacting the round shaped particles in a marumerizer, (a cylindrical vessel with a rotating disk at the bottom) for about 45 to 90 seconds. An alternative method of compacting the microspheres can also be achieved in a rotating conventional coating pan. In this case, the particles are tumbled in the pan for about 15 to 30 minutes, occasionally wetting the particles with a fine mist of the liquid composition and dusting a dry blend of the composition over the liquid wetted microspheres.
6) Drying the spherical particles in an oven under a stream of warm and dry air not exceeding 40° C. and 40% relative humidity.
7) Separating the microspheres according to the desired sizes using U.S. Standard sieve screens.
8) Coating the desired and classified microspheres (for example, in the 14 to 16 mesh and separately in the 20 to 40 mesh size range) with an acid-resistant polymer in fluidized bed coating equipment, or in a conventional coating pan according to standard operating procedures as described in the manufacturer's instruction manual.
9) Drying the acid-resistant polymer coated microspheres in an oven under a stream of warm and dry air not exceeding 40° C. and 40% relative humidity until all the volatile substances (moisture and solvents) are removed.

The following examples will further serve to illustrate the compositions of the present invention wherein the compositions and the process of preparing them will be described with reference to microsphere forms; however, it is to be noted that the microtablet form of the composition and the process of making it is also intended to be covered by the present invention. The process of making the microtablet form of the composition is analogous to that of making the microspheres with the exception that the 40 to 80 mesh particles are compressed together into microtablets of 0.5 mm to 2.5 mm with a suitable tablet press and polymer coated, and should be understood by those skilled in the art.

Example 1
Generalized Formula Composition (polymer coated)

| Ingredients | % w/w |
|---|---|
| Disintegrant | 0.5–16 |
| Buffered-Bile acid (micronized) | 0–20 |
| Buffering agent (anhydrous) | 15–60 |
| Enzymes | 10–70 |
| Adhesive Polymer | 1–19 |
| Polymer coat/talc mixture | 7–25 |

Example 2
PANCRECARB ™ MS-8

| Ingredients | MS-8* w/w |
|---|---|
| Pancreatin (conc.)** | 61.7% |
| Sodium carbonate, Anhydrous, NF | 17.4% |
| Sodium Bicarbonate, NF | 1.7% |
| Sodium starch Glycolate, NF | 3.6% |
| Ursodiol (Pharmacopeial Forum) | 0.9% |
| Polyvinylpyrrolidone, USP | 1.7% |
| Cellulose Acetate Phthalate, NF | 9.8% |
| Diethyl Phthalate, NF | 2.7% |
| Talc, USP | 0.5% |
| | 100% |

*Potency:

| Lipase | 8,000 USP/Cap |
|---|---|
| Amylase | 40,000 USP/Cap |
| Protease | 45,000 USP/Cap |

**Pancreatin conc. with 40 USP units per mg of lipase activity.

Example 3
PANCRECARB ™ MS-4

| Ingredients | % w/w |
|---|---|
| Pancreatin (conc.)** | 39.1% |
| Sodium carbonate, Anhydrous, NF | 17.4% |
| Sodium Bicarbonate, NF | 20.9% |
| Sodium starch Glycolate, NF | 7.0% |
| Ursodiol (Pharmacopeial Forum) | 0.9% |
| Polyvinylpyrrolidone, USP | 1.7% |
| Cellulose Acetate Phthalate, NF | 9.8% |
| Diethyl Phthalate, NF | 2.7% |
| Talc, USP | 0.5% |
| | 100% |

*Potency:

| Lipase | 4,000 USP/Cap |
|---|---|
| Amylase | 25,000 USP/Cap |
| Protease | 25,000 USP/Cap |

**Pancreatin conc. with 40 USP units per mg of lipase activity.

Example 4
PANCRECARB ™ MS-16

| Ingredients | % w/w |
|---|---|
| Disintegrant | 4.0 |
| Ursodiol | 0.9 |
| Buffering agent (anhydrous) | 30.0 |
| Enzymes* | 45.0 |
| Adhesive Polymer | 2.1 |
| Polymer coat/talc mixture | 18.0 |
| | 100.0 |

-continued

**Pancreatin conc. high lipase (>100 USP units per mg activity).
Example 5

| Ingredients | % w/w |
|---|---|
| Buffered-bile acid blend | 1.2 |
| Disintegrant | 4.3 |
| Buffering agent (anhydrous) | 59.5 |
| Enzymes* | 15.0 |
| Adhesive polymer mixture | 3.0 |
| Polymeric coat/talc mixture | 17.0 |

*Pancreatin conc. high lipase (>100 USP units per mg activity).
Example 6

| Ingredients | % w/w |
|---|---|
| Buffered-bile acid (micronized) | 7.5 |
| Disintegrant | 2.0 |
| Buffering agent | 45.0 |
| Adhesive polymer mixture | 9.5 |
| Enzymes* | 20.0 |
| Polymeric coat/talc mixture | 16.0 |
| | 100.0 |

*Pancreatin conc. high lipase (>100 USP units per mg activity).
Example 7 illustrates the composition of the acid-resistant polymer coating.
Example 7

| Ingredients | % w/w |
|---|---|
| Hydroxypropyl methyl cellulose phthalate or cellulose acetate phthalate | 7.5 |
| Diethyl phthalate or dibutyl phthalate | 2.0 |
| 2-Propanol | 45.2 |
| Ethylacetate | 45.2 |
| Talc, USP | 0.1 |

Distribution of the microspheres produced according to the invention was analyzed, the result is shown in Table IV.

TABLE IV

Distribution of the Microspheres According to Sizes

| Mesh Size | (mm) | Example 2 Microspheres (%) | Example 2 Microspheres (%) |
|---|---|---|---|
| 20 | 0.84 | 10.0 | 59.0 |
| 40 | 0.42 | 53.8 | 33.0 |
| 60 | 0.25 | 28.6 | 5.2 |
| 80 | 0.177 | 7.6 | 2.8 |

Raw materials and reagents used in the present invention are well-known and are commercially available or can be made by art-accepted methods. For example, Suitable Disintegrants are available from Mendell, Inc., EXPLOTAB and from Kelco Co., microcrystalline cellulose and propylene glycol alginate.

Suitable Adhesive Polymeric Agents are available: Hydroxypropyl cellulose (Klucel HF, Hercules Co.), polyvinylpyrrolidone (Plasdone, GAF Co.), a 60:40 blend of methyl cellulose and ethyl cellulose (Dow Chem. Co.), Hydroxypropyl methyl cellulose (Grades 50 and 55, Eastman Kodak Co.), cellulose acetate phthalate and hydroxypropyl methyl cellulose phthalate (Eastman Kodak Co.) and propylene glycol alginate (Kelco Co.).

Suitable Acid-Resistant Polymers to coat the microspheres are available: Hydroxypropyl methyl cellulose phthalate, Grades 50 and 55 (Eastman Kodak Co., or Shin-Etsu Chemical Co., Ltd.), Aquateric® aqueous enteric coating polymer dispersion (FMC Corp.), Eudragit® acrylic based polymeric dispersion (Rohm Pharma GMBH, Germany), and cellulose acetate phthalate (Eastman Kodak Co.).

Clinical Observation

All the currently prescribed pancreatic enzyme products lack bicarbonate (buffer) and are dependent on the patient's ability to provide the needed bicarbonate for activity. However, most cystic fibrosis patients are deficient in bicarbonate secretion, and therefore, are unable to provide optimal condition for lipase activity.

The total enzyme activity in chronic pancreatitis patients vs. total enzyme activity in normal patients is shown in Table V.

TABLE V

| | Total Enzyme Activity | | | | | | |
|---|---|---|---|---|---|---|---|
| | Lipase | Trypsin | Chymo-trypsin | Amylase | Pro-tease | Pro-tein | mEq $HCO_3$ |
| Cystic Fibrosis (C.F.) | 121 | 80 | 26 | 145 | 65 | 370 | 1.74 |
| Chronic Pancreatitis | 62,644 | 12,808 | 8,544 | 11,664 | 1,723 | 1,283 | 7.21 |
| Normal | 496,638 | 40,284 | 56,946 | 48,844 | 3,846 | 2,402 | 34.23 |

*60 minutes stimulation period with Secretin/CCK hormones.

Dose response of commercial products based on lipase units per meal was compared with dose response of the present invention based on lipase units per meal. Results are shown in Table VI.

TABLE VI

Dose Response
Lipase Unit/Meal

| Competitive Products Average Dose | Formulation in Example 2 PANCRECARB ™* MS-8 Average Dose |
|---|---|
| 64,000 | 32,000 |
| 120,000 | 64,000 |
| 100,000 | 48,000 |
| 20,000 | 8,000 |
| 24,000 | 24,000 |
| 100,000 | 40,000 |
| 80,000 | 32,000 |
| 100,000 | 24,000 |
| 76,000 ± 37,156 (100%) | 34,000 ± 16,971 (45%) |

*PANCRECARB ™ is a trademark covering compositions of the present invention.

As shown, the dosage of the present invention was more effective even at less than 50% of the lipase dosage of commercial products.

Lipase activity of PANCRECARB™ is shown in Table VIA.

TABLE VIA

Lipase Activity of PANCRECARB ™

| | pH | Label Claim | Assayed Activity at pH 9.0 | Buffering Capacity** | % Activity in the Duodenum at*** pH 7.5–8.5 | |
|---|---|---|---|---|---|---|
| MS-4 | 9.0 | 4000 | 5100 | 2.4 meq | 51% | 89% |
| MS-8 | 9.0 | 8000 | 9800 | 1.5 meq | 47% | 86% |

*pH of ground-up composition dissolved in distilled water
**Buffering Capacity = 1 meq bicarbonate neutralize 12 ml gastric juice form pH 1.5 to pH 7.0
***PANCRECARB ™ as sufficient bicarbonate buffering capacity to raise the duodenal pH's above 7.5 in the microenvironment and ensure greater bioactivity of lipase The present invention identified as PANCRECARB™ MS-8 was comparatively tested against other commercial products in a field trial for 4 weeks. The objective of the study was to monitor gastrointestinal signs and symptoms and quality of life in patients with cystic fibrosis.

The patients received commercial products
    PANCREASE®
    ULTRASE™
    CREON®
    COTAZYME
and product of the present invention. i.e. PANCRECARB™ MS-8 (Example 2).

The composition and pH opf the products are shown in Table VIB.

TABLE VIB

Enteric-Coated Pancreatic Enzyme Containing Products

| PRODUCT | ACTIVE INGREDIENTS | INACTIVE INGREDIENTS | pH |
|---|---|---|---|
| COTAZYME ®-S (Organon) | LIPASE-8,000 USP Units/Cap AMYLASE-30,000 USP Units/Cap PROTEASE-30,000 USP Units/Cap | Cellulose Acetate Phthalte, Dimethyl Phthalate, Calcium Carbonate, Gelatin, Sodium Glycolate, Cornstarch, Talc, FD&C Green #3 And Yellow #10, Titanium Dioxide, Magnesium Stearate | 5.7 |
| PANCRECARB ™ (DCI) | LIPASE-8,000 USP Units/Cap AMYLASE-35,000 USP Units/Cap PROTEASE-35,000 USP Units/Cap | Cellulose Acetate Phthalte, Dimethyl Phthalate, Sodium Carbonate, Sodium Bicarbonate, Povidone, Gelatin, Sodium Starch Glycolate and Talc. | 9.0 |
| CREON ®-10 (Solvay) | LIPASE-10,000 USP Units/Cap AMYLASE-33,200 USP Units/Cap PROTEASE-37,500 USP Units/Cap | Dibutyl Phthalate, Dimethicone, Hydroxypropyl Methylcellulose Phthalate, Light Mineral Oil, Polyethylene Glycol, Gelatin, Titanium Dioxide, Black Iron Oxide, Red Iron Oxide, Yellow Iron Oxide, FD&C Yellow #10 and FD&C Red #40 | 5.5 |
| PANCREASE ® (McNeal) | LIPASE-4,000 USP Units/Cap AMYLASE 20,000 USP Units/Cap PROTEASE-25,000 USP Units/Cap | Cellulose Acetate Phthalate, Diethylphthalate, Gelatin, Povidone, Sodium Starch Glycolate, Corn Starch, Sugar, Talc, Titanium Dioxide | 5.9 |
| ULTRASE ® MT12 (Scandipharm) | LIPASE-12,000 USP Units/Cap AMYLASE-39,000 USP Units/Cap PROTEASE-39,000 USP Units/Cap | Hydrogenated Castor Oil, Silicon Dioxide, Sodium Carboxymethylcellulose, Magnesium Stearate, Cellulose Microcrystalline, Methacrylic Acid Copolymer (Type C), Simethicone, Triethyl Citrate, Iron Oxides, Titanium Dioxide | 5.7 |

Comparative test results are shown in Table VII.

TABLE VII

| Patients | Current Enzyme | Switch To | Stool Frequency | Digestive Symptoms | Patient Remarks |
|---|---|---|---|---|---|
| 1 | PANCREASE ® MT-16 4 caps (64,000 U) | PANCRECARB ™ MS-8 4 caps (32,000 U) | No change* | Less Discomfort | Wants to stay on PANCRECARB ™ |
| 2 | ULTRASE ™ MT-20 6 caps (120,000 U) | PANCRECARB ™ MS-8 8 caps (64,000 U) | No change* | Less Pain | Wants to stay on PANCRECARB ™ |
| 3 | CREON ® 20 5 caps (100,000 U) | PANCRECARB ™ MS-8 6 caps (48,000 U) | No change* | Feels Better | Wants to stay on PANCRECARB ™ |
| 4** | CREON ® 20 1 cap (20,000 U) | PANCRECARB ™ MS-8 1 cap (8,000 U) | No change | No Change | Wants to stay on CREON ® 20 |
| 5** | COTAZYME ™ 8 3 caps (24,000 U) | PANCRECARB ™ MS-8 2 caps (16,000 U) 1 cap COTAZYME ™ (8,000 U) | No change | No Change | Wants to stay on COTAZYME ™ |
| 6 | PANCREASE ® MT-20 5 caps (100,000 U) | PANCRECARB ™ MS-8 5 caps (40,000 U) | No change* | Feel Better | Wants to stay on PANCRECARB ™ |
| 7 | PANCREASE ® MT-16 5 caps (80,000 U) | PANCRECARB ™ MS-8 4 caps (32,000 U) | No change* | No Pain Can sleep overnight, Gained 2½ lbs in 2 wks. | Continue on PANCRECARB ™ |
| 8 | CREON ® 20 5 cps (100,000 U) | PANCRECARB ™ MS-8 3 caps (24,000 U) | Less Diarrhea (4→2) | Less Pain Discharged from Hospital | Continue on PANCRECARB ™ |

*Formed and Bulkier Stool
**Adult Patient
Patients 4 and 5 on PANCRECARB ™ for 24 hours only It is clear from the results in Table VII that PANCRECARB™ MS-8 (Example 2) was more effective at a reduced dose (average 45% to relieve digestion symptoms than the comparative products, i.e., PANCREASE™, ULTRASE™ and CREON™.

The total amount of the composition required to be administered to an enzyme/bile acid, buffer deficient patient will vary with the severity of the conditions, age and other physical characteristics of the patient. The physicians will prescribe the total amount, the dosage and the frequency of dosage administration on a patient by patient basis. Generally, for enzyme/bile acid, buffer deficient patient from about 0.75 to about 1.5 grams of the composition are administered with each major meal, three times a day. Larger amount may, however, be required for certain conditions.

For ease of administration of the compositions it is preferred to use gelatin capsules containing about 0.2 to 0.5 grams microspheres or microtablets. Gelatin capsules which disintegrate in the acidic environment of the stomach are well-known and utilized in the prior art. Microtablets are of small size, having a diameter between about 1 to 1.5 mm and a thickness between 0.5 to 4 mm. The microtablet is prepared by conventional tableting procedure. However, the compositions of the present invention is in the form of very small particle sizes may be used per se. Young children or adults with certain diseases are unable to swallow big gelatin capsules. Microspheres of very small size of the present invention could then be administered to the patients with liquid food, such as milk, apple sauce and semi-solid foods.

Compositions of the present invention containing lipase, amylase and protease were tested for stability at 30° C. (greater than 8,000 USP units/cap) and 40° C. for 104 weeks. The results are shown in Table VIII.

TABLE VIII

STABILITY SUMMARY FOR FORMULA IN EXAMPLE 2

| Weeks Storeage at 30° C.* | Lipase USP Unit/Cap | Amylase USP Unit/Cap | Protease USP Unit/Cap |
|---|---|---|---|
| 0 | 10,880 | 68,000 | 66,400 |
| 4 | 11,520 | 68,000 | 58,000 |
| 8 | 10,760 | 68,000 | 64,000 |
| 12 | 10,240 | 60,800 | 62,400 |
| 24 | 10,320 | 61,600 | 55,600 |
| 104 | 9,720 | 54,400 | 53,760 |

*The results demonstrate at least two year shelf-life stability of the composition described in Example 2 at 30° C.

STABILITY SUMMARY FOR FORMULA IN EXAMPLE 2

| Weeks Storeage at 40° C.** | Lipase USP Unit/Cap | Amylase USP Unit/Cap | Protease USP Unit/Cap |
|---|---|---|---|
| 0 | 10,880 | 68,000 | 66,400 |
| 4 | 10,240 | 66,800 | 60,000 |
| 8 | 9,320 | 63,200 | 62,800 |
| 12 | 8,320 | 60,400 | 60,400 |
| 24 | 8,420 | 55,200 | 58,000 |
| 104 | 7,800 | 54,080 | 60,480 |

**The result at 40° C. demonstrates that greater than 90% of the label claim lipase activity (8,000 USP units/cap) is maintained over two years.

The invention has been described in detail with particular reference to certain preferred embodiments thereof, but it will be understood that variations and modifications can be effected within the spirit and scope of the invention.

What is claimed is:

1. In an improved buffered digestive enzyme composition in the form of microencapsulated particles having a diameter of from about 10 mesh to about 40 mesh for the treatment of digestive enzyme/buffer deficiency of a mammal comprising:

a) from about 10 to about 70% w/w of an enzyme selected from the group consisting of pancreatic proteases, lipases, nucleases and amylases;

b) from about 0.5 to about 16% of a disintegrant selected from the group consisting of ursodiol, starch, modified starches, microcrystalline cellulose and propylene glycol alginate;

c) from about 1 to about 19% w/w of an adhesive polymer selected from the group consisting of polyvinylpyrrolidone, hydroxypropyl cellulose, cellulose acetate phthalate, ethyl cellulose and hydroxypropylmethyl cellulose; and d) from about 7.0 to about 25% w/w of an non-porous, gastric acid-resistant and pharmaceutically acceptable polymer-coating which contains less than 2% talc and which is insoluble in the pH range of from about 1.5 to about 5 but is soluble in the pH range of from about 5.5 to about 9, said polymer-coating comprises a polymer selected from the group consisting of hydroxypropyl methyl cellulose phthalate, cellulose acetate phthalate, diethyl phthalate, dibutyl phthalate, an enteric coating polymeric dispersion, and an acrylic based polymeric dispersion, the improvement consisting essentially of:

from about 45 to 60% w/w of a buffering agent selected from the group consisting of: anhydrous sodium carbonate, sodium bicarbonate, potassium carbonate, potassium bicarbonate, ammonium carbonate, tromethamine, di(tris(hydroxymethyl)amino-methane) carbonate, tris-glycine, di-arginine, tri-arginine, poly-arginine, di-lysine, tri-lysine, poly-lysine, diethylamine and triethanolamine, said buffering agent providing a pH of from 7 to 9 in the small intestine of said mammal, and said lipase having an activity of from 24% to 100% at said pH of from 7 to 9.

2. In an improved buffered digestive enzyme-bile acid composition in the form of microencapsulated particles having a diameter of from about 10 mesh to about 40 mesh for the treatment of digestive enzyme-bile acid-buffer deficiency of a mammal comprising:

a) from about 10 to about 70% w/w of a pancreatic enzyme selected from the group consisting of pancreatic proteases, lipases, nucleases and amylases;

b) from about 0.1 to about 15% w/w of a micropulverized, buffered bile acid in powder form, said buffer/bile acid forming a mixture of a 1 to 1 neutralization equivalent ratio, said buffer is selected from the group consisting of anhydrous sodium carbonate, sodium bicarbonate, potassium carbonate, potassium bicarbonate, ammonium carbonate, tromethamine, di(tris(hydroxymethyl)amino-methane)carbonate, tris-glycine, di-arginine, tri-arginine, poly-arginine, di-lysine, tri-lysine, poly-lysine, diethylamine and triethanolamine;

c) from about 0.5 to about 16% w/w of a disintegrant selected from the group consisting of ursodiol, starch, modified starches, microcrystalline cellulose and propylene glycol alginate;

d) from about 1 to about 19% w/w of an adhesive polymer selected from the group consisting of polyvinylpyrrolidone, hydroxypropyl cellulose, cellulose acetate phthalate, ethyl cellulose and hydroxypropylmethyl cellulose; and e) from about 7.0 to about 25% w/w of an non-porous, gastric acid-resistant and pharmaceutically acceptable polymer-coating which contains less than 2% talc and which is insoluble in the pH range of from about 1.5 to about 5 but is soluble in the pH range of from about 5.5 to about 9, said polymer-coating comprises a polymer selected from the group consisting of hydroxypropyl methyl cellulose phthalate, cellulose acetate phthalate, diethyl phthalate, dibutyl phthalate, an enteric coating polymeric dispersion, and an acrylic based polymeric dispersion;

the improvement consisting essentially of:

from about 45 to 60% w/w of a buffering agent selected from the group consisting of anhydrous sodium carbonate, sodium bicarbonate, potassium carbonate, potassium bicarbonate, ammonium carbonate, tromethamine, di(tris(hydroxymethyl)aminomethane) carbonate, tris-glycine, di-arginine, tri-arginine, poly-arginine, di-lysine, tri-lysine, poly-lysine, diethylamine and triethanolamine, said buffering agent providing a pH of from 7 to 9 in the small intestine of said mammal, and said lipase having an activity of from 24% to 100% at said pH of from 7 to 9.

3. The improved buffered digestive enzyme-bile acid composition of claim 2 wherein 0.25 to 10% w/w of said micropulverized, buffered bile acid is present in the composition.

4. In an improved method for treating digestive enzyme, bile acid and buffer deficiency in a mammal comprising orally administering an effective amount of a composition comprising:

a) from about 10 to about 70% w/w of a concentrate of an enzyme selected from the group consisting of pancreatic proteases, lipases, nucleases and amylases;

b) from about 0.5 to about 16% of a disintegrant selected from the group consisting of ursodiol, starch, modified starches, microcrystalline cellulose and propylene glycol alginate;

c) from about 1 to about 19% w/w of an adhesive polymer selected from the group consisting of polyvinylpyrrolidone, hydroxypropyl cellulose, cellulose acetate phthalate, ethyl cellulose and hydroxypropylmethyl cellulose; and d) from about 7.0 to about 25% w/w of an non-porous, gastric acid-resistant and pharmaceutically acceptable polymer-coating which contains less than 2% talc and which is insoluble in the pH range of from about 1.5 to about 5 but is soluble in the pH range of from about 5.5 to about 9, said polymer-coating comprises a polymer selected from the group consisting of hydroxypropyl methyl cellulose phthalate, cellulose acetate phthalate, diethyl phthalate, dibutyl phthalate, an enteric coating polymeric dispersion, and an acrylic based polymeric dispersion;

the improvement consisting essentially of:

from about 45 to 60% w/w of a buffering agent selected from the group consisting of: anhydrous sodium carbonate, sodium bicarbonate, potassium carbonate, potassium bicarbonate, ammonium carbonate, tromethamine, di(tris(hydroxymethyl)aminomethane) carbonate, tris-glycine, di-arginine, tri-arginine, poly-arginine, di-lysine, tri-lysine, poly-lysine, diethylamine and triethanolamine, said buffering agent providing a pH of from 7 to 9 in the small intestine of said mammal, and said lipase having an activity of from 24% to 100% at said pH of from 7 to 9.

5. The improved method of claim 4 wherein said digestive enzyme, bile acid and buffer deficiency treatment is to reduce or modify conditions in a mammal selected from the group consisting of: digestive enzyme deficiency, digestive disorders, impaired liver function, cystic fibrosis and presence of gallstones.

* * * * *